United States Patent
Ergler et al.

(10) Patent No.: US 11,076,822 B2
(45) Date of Patent: Aug. 3, 2021

(54) PHOTON DETECTOR, METHOD FOR PRODUCING A PHOTON DETECTOR, AND X-RAY APPARATUS

(71) Applicant: Siemens Healthcare GmbH, Erlangen (DE)

(72) Inventors: Thorsten Ergler, Erlangen (DE); Michael Hosemann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 60 days.

(21) Appl. No.: 16/689,540

(22) Filed: Nov. 20, 2019

(65) Prior Publication Data

US 2020/0170593 A1  Jun. 4, 2020

(30) Foreign Application Priority Data

Dec. 3, 2018  (EP) .................................... 18209798

(51) Int. Cl.
*A61B 6/00* (2006.01)
*G01T 1/24* (2006.01)
(Continued)

(52) U.S. Cl.
CPC .......... *A61B 6/4233* (2013.01); *A61B 6/4241* (2013.01); *G01T 1/24* (2013.01);
(Continued)

(58) Field of Classification Search
CPC ....... A61B 6/4241; A61B 6/4233; G01T 1/24; G01T 1/2928; H01L 27/14659; H01L 27/14636
See application file for complete search history.

(56) References Cited

U.S. PATENT DOCUMENTS

2016/0015339 A1  1/2016  Danzer et al.
2016/0116610 A1  4/2016  Labayen de Inza et al.
(Continued)

FOREIGN PATENT DOCUMENTS

CN  105556673 A  5/2018
DE  102007022197 A1  4/2008
(Continued)

OTHER PUBLICATIONS

European Office Action dated May 26, 2021.

*Primary Examiner* — Michael C Bryant
(74) *Attorney, Agent, or Firm* — Harness, Dickey & Pierce, P.L.C.

(57) ABSTRACT

A photon detector includes at least one sensor element, formed by a semiconductor material and sensitive to incident radiation, forming a pixel array including sensor pixels; and a detector circuit, situated after the sensor element in the direction of incident radiation, to detect charge carriers generated in the semiconductor material as a result of radiation. The detector circuit includes an integrated circuit with detector pixels in signal communication contact with the sensor pixels; and an enclosure surrounding the integrated circuit and in which the integrated circuit is embedded, and on which is formed on a pixel face facing the sensor element. A contact redistribution layer is formed, in which contact pads are formed for signal-communicatively connecting the detector pixels to the correspondingly assigned sensor pixels, and also conductor tracks are formed for connecting the contact pads to the detector pixels of the integrated circuit.

23 Claims, 4 Drawing Sheets

(51) Int. Cl.
*H01L 27/146* (2006.01)
*G01T 1/29* (2006.01)

(52) U.S. Cl.
CPC ............ *G01T 1/247* (2013.01); *G01T 1/2928* (2013.01); *H01L 27/14636* (2013.01); *H01L 27/14659* (2013.01)

(56) References Cited

U.S. PATENT DOCUMENTS

| | | | |
|---|---|---|---|
| 2016/0154124 A1* | 6/2016 | Luhta | H01L 27/14618 250/361 R |
| 2017/0227658 A1* | 8/2017 | Steadman Booker | A61B 6/4208 |
| 2018/0120447 A1 | 5/2018 | Ergler et al. | |

FOREIGN PATENT DOCUMENTS

| | | |
|---|---|---|
| DE | 102014213734 A1 | 2/2016 |
| DE | 102014221829 A1 | 4/2016 |
| DE | 102016201808 A1 | 8/2017 |
| DE | 102016221481 A1 | 5/2018 |

\* cited by examiner

PHOTON DETECTOR, METHOD FOR PRODUCING A PHOTON DETECTOR, AND X-RAY APPARATUS

PRIORITY STATEMENT

The present application hereby claims priority under 35 U.S.C. § 119 to European patent application number EP 18209798.0 filed Dec. 3, 2018, the entire contents of each of which are hereby incorporated herein by reference.

FIELD

Embodiments of the invention generally relate to a photon detector, in particular to an X-ray radiation detector. Embodiments of the invention also generally relate to a method for producing the photon detector and to a medical X-ray apparatus comprising the photon detector.

BACKGROUND

Photon detectors are regularly used in addition to conventional cameras (photographic equipment or moving-image cameras) in (preferably medical) X-ray imaging apparatuses. Conventional photon detectors comprise a layer of scintillator material (usually a ceramic), which layer is sensitive to X-ray radiation and in which incident X-ray radiation is converted into radiation in the visible spectral region. This visible radiation is detected on the reverse side from the incident X-ray radiation by photodiodes, CMOS sensors or the like, and evaluated in order to generate the X-ray image. In this process, the visible radiation is detected at relatively long time intervals, during which the incident X-ray radiation is effectively integrated.

What are known as quantum-counting or photon-counting photon detectors are in development or even already in use in order to reduce the X-ray dose in particular for patients. This detector uses a semiconductor material, for instance cadmium telluride (CdTe for short), as the layer (called the "sensor element") that is sensitive to (X-ray) radiation. In this material, the incident (X-ray) radiation, specifically each incident (X-ray) photon, generates a number of charge carriers (in particular a plurality of electron-hole pairs), which, as a result of a (high) voltage applied to the sensor element, drift to a planar face of the sensor element, and are detected there by an evaluation circuit in contact with the sensor element.

In order to allow spatial resolution of the detected events, the sensor element is divided into a plurality of image points (referred to below as "sensor pixels") arranged in the form of a grid. The evaluation circuit comprises "detector pixels", one assigned to each sensor pixel for the purpose of detection, and each in signal communication contact with the associated sensor pixel. The evaluation circuit is usually in the form of an integrated circuit, specifically an application-specific circuit (ASIC).

To be able to minimize noise and provide high image quality, these integrated circuits must be coupled to the sensor pixels by the shortest possible distance. Typically, however, the area spanned by the sensor element and the individual sensor pixels thereof is larger than the ASIC area that, thanks to modern fabrication technologies, is needed to evaluate these sensor pixels. Yet to be able to provide the shortest possible distance to the sensor pixels, the geometry of the detector pixels and hence of the associated ASIC is aligned with the geometry of the sensor element and hence with the array formed by the sensor pixels. This in turn increases the costs of the ASICs. Furthermore, in order to be able to make contact between the particular ASIC and a subsequent conduction plane, power supply, or the like, it is necessary to introduce complicated and hence costly vias (known as "through-silicon vias", "TSVs") into the ASIC.

Document DE 10 2014 213 734 A1 discloses an imaging device for electromagnetic radiation, in particular for X-ray and/or gamma radiation, which comprises a layered arrangement composed of a number of detection elements, a number of readout circuit boards, and a base circuit board, wherein the, or each, detection element is in electrical contact with an associated readout circuit board via a plurality of first solder bonds, wherein the, or each, readout circuit board comprises a plurality of vias, and wherein the, or each, readout circuit board is in electrical contact with the base circuit board via a plurality of second solder bonds.

Document DE 10 2014 221 829 A1 discloses a method for producing a sensor board for a detector module, wherein a plurality of readout units are provided, wherein the readout units are positioned one at a time in a stacked arrangement on a shared sensor layer, and wherein once all the readout units have been positioned, they are fixed jointly to the sensor layer, forming a hybrid in the process.

DE 10 2016 221 481 A1 discloses a radiation detector having an intermediate layer arranged between a detector layer comprising a number of detection elements and a number of readout units. The intermediate layer comprises a multiplicity of electrically conducting connections between the detection elements and the readout units.

SUMMARY

Embodiments of the invention are directed to a photon detector; a method for producing a photon detector; and an X-ray apparatus. The claims and the description below present further advantageous embodiments and developments of the invention, some of which are inventive in their own right.

The photon detector according to at least one embodiment of the invention preferably constitutes an X-ray radiation detector. The photon detector comprises for this purpose at least one sensor element, which is formed by a semiconductor material and is sensitive to incident radiation, preferably X-ray radiation. In addition, this sensor element forms a pixel array (also called a "sensor array") comprising, more specifically consisting of, a number of sensor pixels. The photon detector also comprises a detector circuit (in particular at least one detector circuit), which is situated after the sensor element in the direction of incident radiation, and which is used to detect charge carriers generated in the semiconductor material of the sensor element as a result of radiation. The detector circuit comprises an integrated circuit (abbreviated below to "ASIC"), which in turn comprises a number of detector pixels corresponding in particular to at least a subset of the sensor pixels. These detector pixels are in signal communication contact with the sensor pixels (at least with the subset). In this case, however, a surface dimension (i.e. at least one edge length) of the ASIC is smaller than the surface dimension (i.e. the corresponding edge length) of the sensor element by more than one pixel width of the sensor pixels, preferably by more than two, three or four pixel widths. The detector circuit comprises an enclosure, which surrounds the ASIC and in which the ASIC is embedded. A contact redistribution layer is formed, preferably integrally applied, on a contact face (referred to below as the "pixel face") of the enclosure that faces the sensor element (and preferably also on the ASIC itself). In this contact redistribution layer contact pads are formed for signal-communicatively (in particular galvanically) connecting the detector pixels to the correspondingly assigned sensor pixels, and also conductor tracks for connecting these contact pads to the detector pixels of the ASIC. The purpose of this contact redistribution layer is in particular to expand the contact area of the ASIC, which contact area faces the sensor element and carries contact pads assigned to each detector pixel, outwards over the surface to a (in particular rear) mating contact area of the sensor element that faces this ASIC.

At least one embodiment of the invention also relates to a method for producing the photon detector described above in at least one embodiment, in particular the X-ray radiation detector. According to at least one embodiment of the method, the sensor element described above, which is formed by the semiconductor material and is sensitive to incident radiation, is first provided. The sensor element constitutes the pixel array described above composed of the number of, in particular the multiplicity of, sensor pixels. In addition, the detector circuit described above is provided. The detector circuit is placed after the sensor element in the direction of incident radiation. In other words, the detector circuit is positioned with respect to the sensor element in particular such that it is arranged on a face (designated the rear face) of the sensor element that faces away from a (X-ray) radiation source. The detector circuit is selected such that the integrated circuit, specifically the ASIC described above of the detector circuit, which ASIC comprises a number of detector pixels corresponding to at least a subset of the sensor pixels, in terms of its surface dimension is smaller than the surface dimension of the sensor element by more than one pixel width, preferably by more than two, three, four or more pixel widths of the sensor pixels. Furthermore, the detector pixels of the ASIC are placed in signal communication contact with the sensor pixels (at least with the associated subset of sensor pixels) by way of the contact redistribution layer arranged on the enclosure in which the ASIC is embedded.

At least one embodiment of the invention also relates to a medical X-ray apparatus, which comprises the photon detector described above in at least one embodiment, preferably the X-ray radiation detector formed thereby. For example, this X-ray apparatus is a computed tomography apparatus, a C-arm X-ray apparatus, or the like.

At least one embodiment of the invention also relates to a medical X-ray apparatus which comprises the photon detector described above, preferably the X-ray radiation detector formed thereby, wherein the X-ray apparatus is a computed tomography apparatus.

BRIEF DESCRIPTION OF THE DRAWINGS

Example embodiments of the invention are presented in greater detail below with reference to a drawing, in which.

Corresponding parts are consistently denoted by the same reference signs in all the figures.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The photon detector according to at least one embodiment of the invention preferably constitutes an X-ray radiation detector. The photon detector comprises for this purpose at least one sensor element, which is formed by a semiconductor material and is sensitive to incident radiation, preferably X-ray radiation. In addition, this sensor element forms a pixel array (also called a "sensor array") comprising, more specifically consisting of, a number of sensor pixels. The photon detector also comprises a detector circuit (in particular at least one detector circuit), which is situated after the sensor element in the direction of incident radiation, and which is used to detect charge carriers generated in the semiconductor material of the sensor element as a result of radiation. The detector circuit comprises an integrated circuit (abbreviated below to "ASIC"), which in turn comprises a number of detector pixels corresponding in particular to at least a subset of the sensor pixels. These detector pixels are in signal communication contact with the sensor pixels (at least with the subset). In this case, however, a surface dimension (i.e. at least one edge length) of the ASIC is smaller than the surface dimension (i.e. the corresponding edge length) of the sensor element by more than one pixel width of the sensor pixels, preferably by more than two, three or four pixel widths. The detector circuit comprises an enclosure, which surrounds the ASIC and in which the ASIC is embedded. A contact redistribution layer is formed, preferably integrally applied, on a contact face (referred to below as the "pixel face") of the enclosure that faces the sensor element (and preferably also on the ASIC itself). In this contact redistribution layer contact pads are formed for signal-communicatively (in particular galvanically) connecting the detector pixels to the correspondingly assigned sensor pixels, and also conductor tracks for connecting these contact pads to the detector pixels of the ASIC. The purpose of this contact redistribution layer is in particular to expand the contact area of the ASIC, which contact area faces the sensor element and carries contact pads assigned to each detector pixel, outwards over the surface to a (in particular rear) mating contact area of the sensor element that faces this ASIC.

By using the enclosure and the contact redistribution layer arranged thereon, an ASIC that is smaller than the sensor element, at least smaller than the mating contact area, can hence be employed as the detector circuit. It is hence advantageously possible to avoid (at least material-related) production costs of relatively large-area ASICS. In addition, space can be made for providing interconnects from the ASIC concerned to signal-routing device(s) arranged after the ASIC in the direction of incident radiation, to a higher-level control and analysis unit, and/or to a power supply unit, so that it is possible to dispense with costly vias through the ASIC itself (in particular in the form of TSVs).

Moreover, the detector circuit formed by the ASIC and the enclosure can be signal-communicatively connected to the sensor element also in particular directly, preferably by way of the contact redistribution layer. It is hence possible to dispense with additional (for instance soldered) connecting of the ASIC to an interposed, separate interconnection element (for instance what is known as an interposer). Particularly high fabrication precision can hence be achieved in particular by eliminating additional signal connections (for instance soldered connections to the separate interconnection element). In addition, the positioning of each detector circuit with respect to the corresponding sensor element is also simplified because these are joined directly to one another.

In a preferred embodiment, the ASIC is embedded in the enclosure (which is preferably formed by a casting resin) flush with the surface and without any gaps along its edges (that run perpendicular to the pixel face). This means that the enclosure surrounds the ASIC along the edge faces, and if applicable also on the rear face that faces away from the pixel face.

In principle, various bonding techniques for creating an electrically conducting connection (for instance soldering, conductive adhesive bonding and the like) are conceivable for the signal communication connection of the detector circuit to the sensor element, so specifically of the contact pads assigned to the detector pixels to the corresponding sensor pixels. In the case of a solder connection, however, lead-free low-temperature solders are preferably used in order to avoid thermal damage to the enclosure.

In an expedient embodiment, the contact redistribution layer is formed by a thin film application process. For example, the contact redistribution layer is formed using a vapor phase deposition process (for example at least to form metallization seeds), e.g. PVD (physical vapor deposition), a mask illumination process, or the like, or a combination thereof.

In a preferred embodiment, a process called "fan-out wafer-level chip-scale packaging" is used to fabricate the detector circuit through the ASIC. In this case, the detector circuit therefore forms a component which comprises the ASIC, the enclosure surrounding the ASIC, and the at least one contact redistribution layer. Such detector circuits or components can be purchased as prefabricated elements or even custom-produced if applicable. Manufacturing costs can thereby be saved advantageously compared with the relatively large-area ASICS described above, which are adapted to fit the area of the sensor element. It also makes it possible, even for different photon detectors comprising sensor elements of differing geometry, to use always the same ASIC in conjunction with just an enclosure adapted to fit the relevant sensor element and contact redistribution layer also adapted to fit accordingly. Thus this allows the use of identical parts across different photon detectors, which in turn helps to save costs.

In a particularly expedient embodiment, the detector circuit comprises in the region of the enclosure at least one via, which preferably extends from the pixel face to the rear face, or "connection face", of the detector circuit that faces away from this pixel face. This via is used here for the signal-communication connection of the ASIC to a subsequent control and analysis unit and/or subsequent signal-routing device(s), or the like. In other words, the ASIC of the particular detector circuit is not itself provided with one or more vias (in particular a TSV). This can again save production costs for the detector circuit, because it is possible to dispense with costly vias, specifically known as TSVs, through the ASIC. In contrast, the vias through the enclosure, which is preferably made of plastic, can be produced using comparatively simple and inexpensive production techniques, for instance laser drilling, primary forming, or the like.

Furthermore, the via, or each via, is connected to the ASIC by way of the contact redistribution layer or an additional contact redistribution layer. Conducting structures, for instance conductor tracks, wires, or the like, which are routed around the outer edges of the ASIC or of the enclosure itself from the pixel face to the rear face, can also be avoided by way of the via, or each via, thereby minimizing the overall size of the detector circuit as far as possible. This specifically allows a plurality of sensor elements and detector circuits arranged thereon to be positioned as close as possible side by side, because no space needs to be kept for conducting structures routed via the edges.

In a preferred embodiment, a plurality of detector circuits (for example four) are assigned to one sensor element. The detector circuits are arranged on, and make contact with, the mating contact area of the sensor element in a grid formation. In this embodiment, each ASIC makes contact with one separately assigned group of sensor pixels.

In a further preferred embodiment, the photon detector comprises a plurality of sensor elements arranged side by side, which in particular span a sensor area of the photon detector. The photon detector accordingly also comprises a plurality of the detector circuits described above. Preferably again in this case, a plurality of detector circuits are assigned to each sensor element. The enclosures of at least two (in particular mutually adjacent) detector circuits, preferably of at least four, preferably of a multiplicity of detector circuits, optionally of all the detector circuits, are in this case formed together integrally, in particular monolithically (i.e. from the same material and in a joint fabrication process without forming separation points between the individual "notional" enclosure borders). In other words, the respective ASICS are embedded jointly in an "overall enclosure" and form a relatively large-area integrated "detector circuit array", so that it is possible to dispense with diced detector circuits in the form of separate, encapsulated "chips". It is fundamentally possible here for a plurality of sensor elements and the correspondingly assigned detector circuits to be combined in groups (for example what are known as sensor boards), the detector circuits of which are integrally joined to one another. In this case, a plurality of separate sensor elements are preferably placed on the detector circuit array. Alternatively, however, the corresponding sensor elements can also be integrally, in particular monolithically, joined to one another. The use of the sensor boards (in particular using an integrated detector circuit array) allows, for example, relatively large detector areas to be produced relatively easily by concatenating the sensor boards.

Alternatively and/or depending on the size of the total detector area of the photon detector, all the detector circuits of the photon detector are formed using a shared overall enclosure. In particular, a plurality of separate sensor elements are again placed on a "full area" integrated "detector circuit array" of this type.

By using an overall enclosure, which encompasses all, or at least groups, of the detector circuits, to group the detector circuits, it is also advantageously possible to increase the precision of the alignment of the sensor elements with the associated detector circuits, or at least to simplify a sufficiently precise fabrication process.

For example, in order to produce the groups of detector circuits described above using an overall enclosure, all the ASICs, or at least ASICs verified as "good", fabricated from a common wafer can be embedded in the shared enclosure. In particular in the case of fan-out wafer-level chip-scale packaging, it is thus optionally possible to dispense with separating the individual "chips" after joint embedding of the ASICs in the packaging compound. An option here is to design the shared enclosure to be the size of a single sensor board (in particular composed of a plurality of sensor elements) say of size 2×4 cm$^2$ (which in this case comprises in particular two sensor elements say of area 2×2 cm$^2$ and preferably a plurality of assigned ASICs each) and larger, up to panels of the size of a complete X-ray detector of say 40×40 cm$^2$, in which are embedded a correspondingly high number of ASICs.

In a further preferred embodiment, the detector circuit, or each detector circuit, is configured to identify what is known as a charge-sharing event. For this purpose, adjacent detector pixels of the associated ASIC are signal-communicatively interconnected. It is thereby possible to detect situations in which charge carriers generated by a photon in a specific sensor pixel are also registered by the detector pixels of adjacent sensor pixels. Contact between the adjacent detector pixels is preferably made, for instance, via wiring planes of the associated ASIC, which is typically formed by a CMOS fabrication process. If such charge-sharing events are identified, they can be taken into account in an evaluation of the incident radiation, and in particular can be corrected when generating an image. This in turn increases the precision, in particular the spatial and/or energy resolution of the generated image. Furthermore, what are known as "K escapes" can also be detected in this way. In these cases, radiation is typically regenerated inside the sensor element itself, in particular as a result of processes that refill the K shell of the semiconductor material, which can in turn result in charge carriers being produced in the same sensor pixel or in particular in adjacent sensor pixels. This can cause distortion in the image generation.

In a preferred development, in order to identify such a charge-sharing event (in particular between two adjacent sensor pixels), detector pixels of two ASICs arranged side by side in integrally joined enclosures, which detector pixels face one another along the edges, are also in contact with one another. Contact is made in this case via the, or an additional, contact redistribution layer of the (integrally joined) enclosure, i.e. of the shared enclosure. This use of the contact redistribution layer of the integrally joined enclosure (i.e. of the shared enclosure) in order to make contact between the individual detector pixels and to connect the detector pixels across ASIC borders, advantageously allows a higher link speed, in particular as a result of relatively small parasitic impedances especially in comparison with using bond wires and/or through-silicon vias. Likewise, by way of the contact redistribution layer, the corresponding signal lines can also be made relatively small and hence at a high track density, so that the total amount of space occupied by the detector circuit concerned can be reduced. This embodiment also constitutes a separate invention.

In a further expedient embodiment, two ASICs, which are arranged side by side in integrally joined enclosures, are signal-communicatively connected to one another using the, or an additional, contact redistribution layer of their enclosure (i.e. of their shared enclosure). This contact between two ASICs is used (optionally in addition to the identification of charge-sharing events described above) for instance for clock distribution between the individual ASICS and/or for joint configuration of the individual ASICs. The small parasitic impedance of the conductor tracks of the contact redistribution layer, the small amount of space they occupy, etc. is again exploited advantageously here. Furthermore, using the contact redistribution layer can save on line complexity, for example on a carrier circuit board arranged spatially after the detector circuits.

In a preferred embodiment, the photon detector described above is used as what is known as a flat-panel detector in an X-ray apparatus.

At least one embodiment of the invention also relates to a method for producing the photon detector described above in at least one embodiment, in particular the X-ray radiation detector. According to at least one embodiment of the method, the sensor element described above, which is formed by the semiconductor material and is sensitive to incident radiation, is first provided. The sensor element constitutes the pixel array described above composed of the number of, in particular the multiplicity of, sensor pixels. In addition, the detector circuit described above is provided. The detector circuit is placed after the sensor element in the direction of incident radiation. In other words, the detector circuit is positioned with respect to the sensor element in particular such that it is arranged on a face (designated the rear face) of the sensor element that faces away from a (X-ray) radiation source. The detector circuit is selected such that the integrated circuit, specifically the ASIC described above of the detector circuit, which ASIC comprises a number of detector pixels corresponding to at least a subset of the sensor pixels, in terms of its surface dimension is smaller than the surface dimension of the sensor element by more than one pixel width, preferably by more than two, three, four or more pixel widths of the sensor pixels. Furthermore, the detector pixels of the ASIC are placed in signal communication contact with the sensor pixels (at least with the associated subset of sensor pixels) by way of the contact redistribution layer arranged on the enclosure in which the ASIC is embedded.

At least one embodiment of the method for producing the photon detector likewise includes in particular the advantages arising from the features of the photon detector described above.

In a preferred embodiment, the process called fan-out wafer-level chip-scale packaging is used to fabricate the detector circuit comprising the ASIC, preferably starting from the ASIC. In this case, the detector pixels are thus advantageously electrically in signal communication contact with the sensor pixels by way of the contact redistribution layer described above, and preferably by way of "solder balls" applied thereto.

At least one embodiment of the invention also relates to a medical X-ray apparatus, which comprises the photon detector described above in at least one embodiment, preferably the X-ray radiation detector formed thereby. For example, this X-ray apparatus is a computed tomography apparatus, a C-arm X-ray apparatus, or the like.

At least one embodiment of the invention also relates to a medical X-ray apparatus which comprises the photon detector described above, preferably the X-ray radiation detector formed thereby, wherein the X-ray apparatus is a computed tomography apparatus.

The "and/or" conjunction shall be understood here and below in particular in the sense that the features linked by this conjunction can be provided both jointly and also as alternatives to one another.

Figure 1:
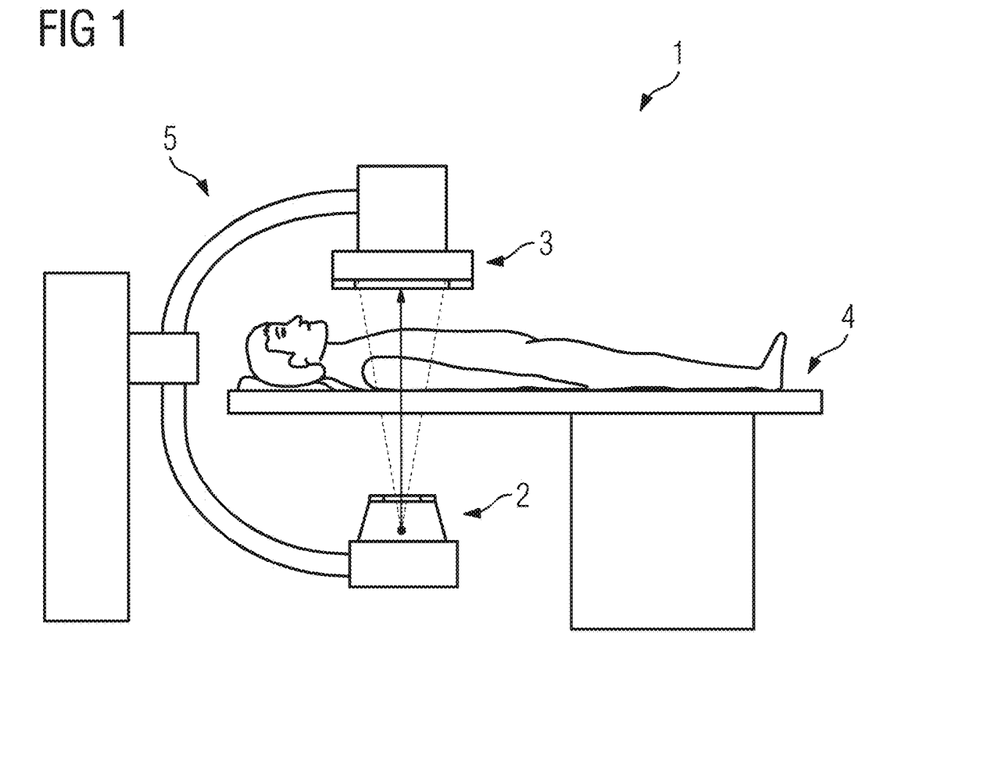
FIG. 1 is a schematic side view of an X-ray apparatus comprising an X-ray radiation source and an X-ray detector.

FIG. 1 shows schematically an X-ray apparatus 1. This X-ray apparatus 1 is specifically what is known as a C-arm X-ray apparatus. The X-ray apparatus 1 comprises an X-ray radiation source 2, which is arranged facing an X-ray radiation detector (X-ray detector 3 for short). The X-ray detector 3 constitutes a photon detector for detecting X-ray photons emitted by the X-ray radiation source 2. The X-ray detector 3 is embodied here as a flat-panel detector. The X-ray apparatus 1 also comprises a patient couch 4 and a handling unit 5, on which the X-ray system composed of the X-ray radiation source 2 and the X-ray detector 3 is arranged for rotation about the patient couch 4.

Figure 6:
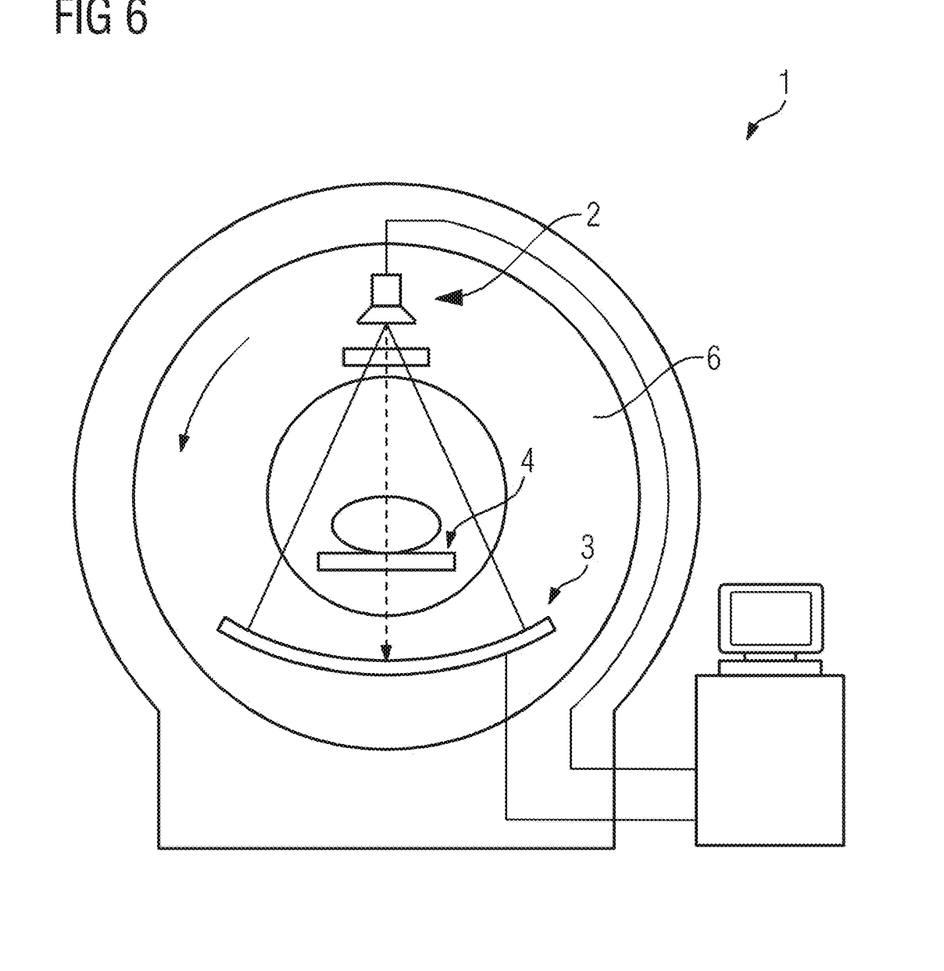
FIG. 6 is a schematic view of a further example embodiment of the X-ray apparatus in the form of a computed tomography apparatus.

FIG. 6 shows an X-ray apparatus 1 comprising a computed tomography apparatus. In this case, the X-ray apparatus 1 constitutes a computed tomography apparatus, with the X-ray system mounted on a rotating assembly 6 for rotation about the patient couch 4. The patient couch 4 can be moved along its longitudinal extent into a tunnel formed by the rotating assembly 6.

The X-ray detector 3 is embodied as a so-called photon-counting or quantum-counting detector (both in the case of the C-arm X-ray apparatus and in the case of the computed tomography apparatus). For this purpose, the X-ray detector 3 comprises a sensor element 10 made of a material that is sensitive to incident X-ray radiation, specifically made of a semiconductor material, in this case cadmium telluride. This sensor element 10 is specifically formed by a board made of this semiconductor material. In addition, the sensor element 10 constitutes a pixel array composed of a multiplicity of individual sensor pixels 12. As shown schematically in FIG. 3, the individual sensor pixels 12 are arranged in a grid formation (i.e. in a regular formation). Specifically, the sensor pixels 12 are formed by mutually separate contact pads, which are applied to a rear face that faces away from an incident radiation face 14 of the sensor element 10 (see FIG. 2).

Figure 2:
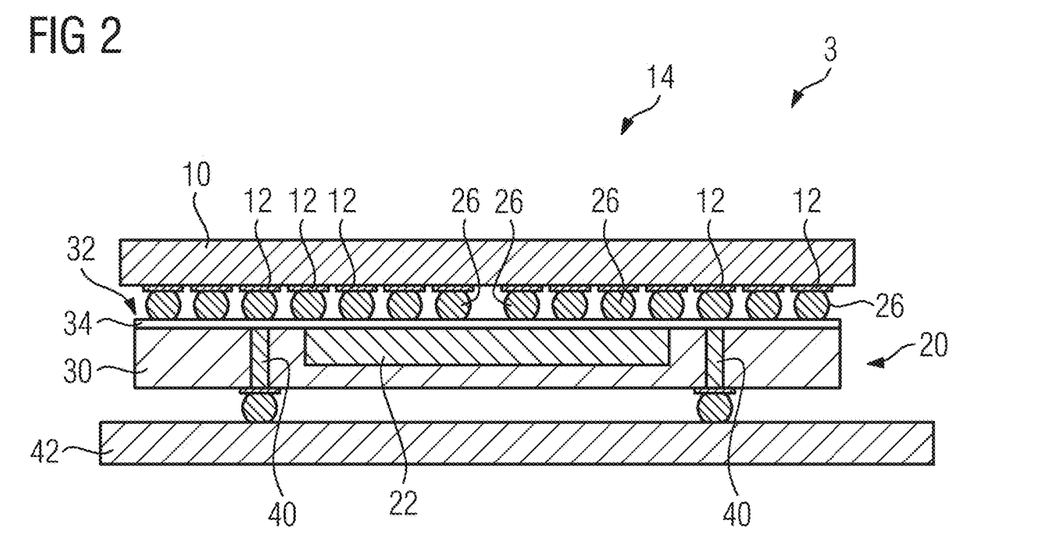
FIG. 2 is a schematic cross-section of a segment of the X-ray radiation detector.

Incident X-ray photons entering the sensor element 10 produce corresponding charge carriers, specifically electron-hole pairs, in the semiconductor material of the sensor element 10. As a result of a high voltage applied between the incident radiation face 14 and the rear face, the charge carriers (at least the negative or positive charge carriers, depending on the applied high voltage) drift to the rear face, and can be detected there by the contact pads assigned to the respective sensor pixels 12.

For the purpose of registering, i.e. detecting, the charge carriers, the X-ray detector 3 comprises a detector circuit 20 situated after the sensor element 10. Apart from detecting the charge carriers, this detector circuit 20 is also used for preprocessing (for instance by a kind of filtering by a threshold comparison) the sensor signals generated when the individual charge carriers are detected. The detector circuit 20 comprises for this purpose an integrated circuit, specifically an ASIC 22. In one variant, the ASIC 22 comprises for each sensor pixel 12 of the associated sensor element 10 a corresponding detector pixel 24 (see FIG. 3). Each of the detector pixels 24 is in signal communication contact with an associated sensor pixel 12. In FIG. 2, individual solder balls 26 indicate this contact by way of example.

Figure 3:
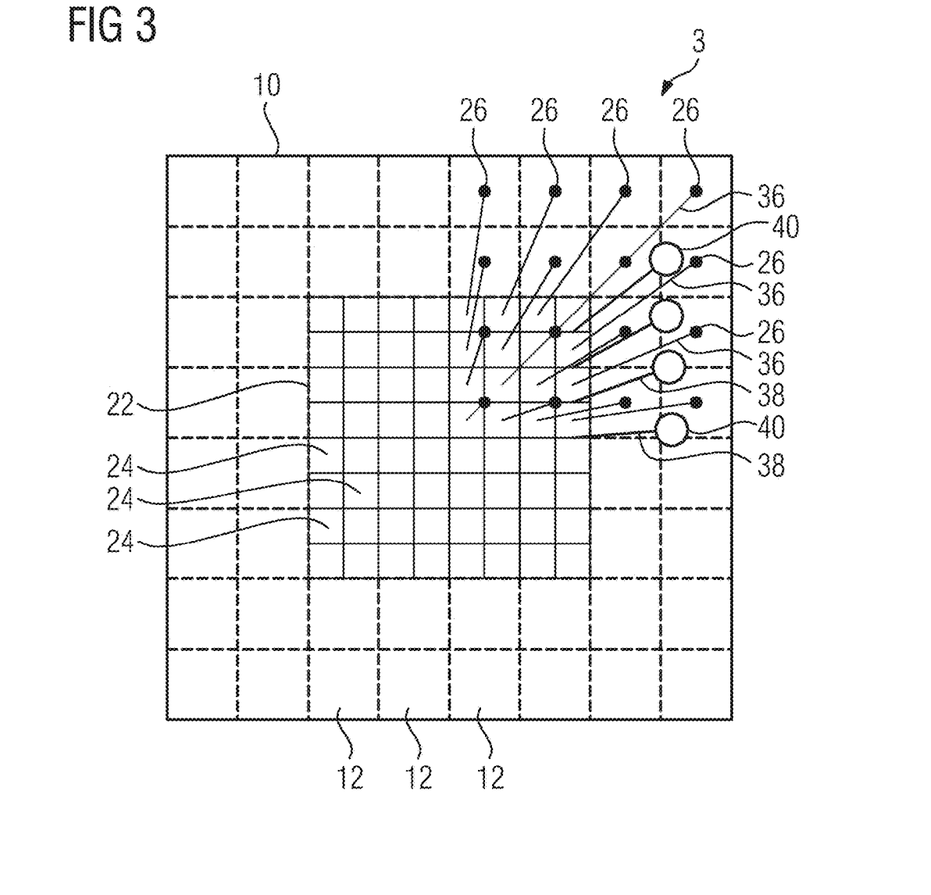
FIG. 3 is a schematic view of a top face of a sensor element of the X-ray radiation detector.

In order to be able to fabricate the associated ASIC 22 as compactly and hence as economically as possible, a surface dimension of the ASIC 22, specifically an edge length of the ASIC 22, is smaller than the surface dimension of the sensor element 10, specifically its corresponding edge length, by at least one pixel width of a sensor pixel 12. As shown in FIG. 3, the edge length of the ASIC 22 is smaller than the edge length of the sensor element 10 by four pixel widths of the sensor pixels 12. For it to be possible nonetheless for the individual detector pixels 24 to make contact with the sensor pixels 12 that extend beyond the area of the ASIC 22, the detector circuit 20 also comprises an enclosure 30, in which the ASIC 22 is embedded. The enclosure 30 is specifically a "block" made of potting compound, specifically a casting resin, in which the ASIC 22 is embedded flush with the surface. For the contact-making, specifically for redistributing the lines from the individual detector pixels 24 to the individual sensor pixels 12, a contact redistribution layer 34 is applied to a pixel face 32 of the detector circuit 20 that faces the sensor element 10.

As shown in FIG. 3, the contact redistribution layer 34 comprises a number of conductor tracks 36, which lead from the individual detector pixels 24 to the solder balls 26. In addition, the contact redistribution layer 34 also comprises conductor tracks 38, which lead from additional circuit structures (not presented in further detail) of the ASIC 22 to vias 40. The vias 40 are formed in the enclosure 30 itself and thus lead solely through a compound made of plastic. The vias 40 are used here for providing the connection (i.e. for making signal communication contact) between the ASIC 22 and subsequent signal routing device(s), which in the present example embodiment are formed by a printed circuit board 42.

The contact redistribution layer 34 is applied to the pixel face 32 of the detector circuit 20 by vapor phase deposition processes, inter alia. The detector circuit 20 is produced by the fan-out wafer-level chip-scale packaging process.

Figure 4:
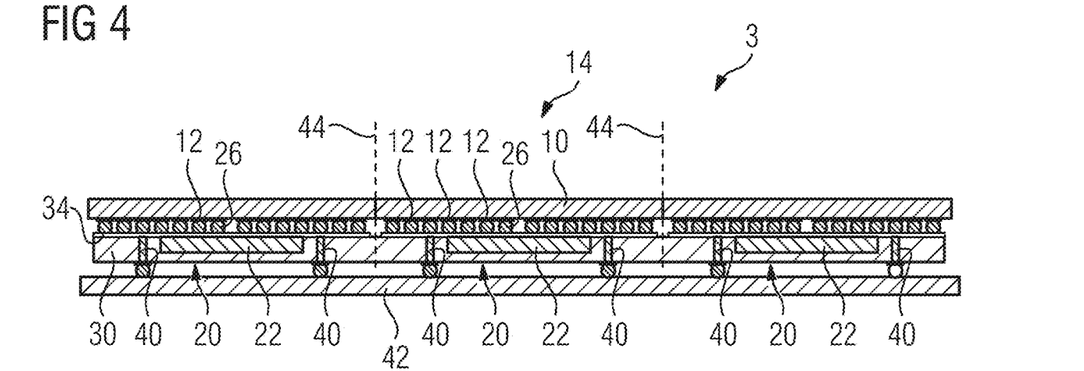
FIG. 4 is a view corresponding to FIG. 2 of a further example embodiment of the X-ray radiation detector.

FIG. 4 shows a further example embodiment in greater detail. In this case, the sensor element 10 of the X-ray detector 3 comprises a larger number of sensor pixels 12 than a single ASIC 22 and thus a plurality of assigned detector circuits 20. The assigned detector circuits 20 are integrally joined to one another in this case by way of their enclosure 30. In other words, the ASICs 22 shown in cross-section in FIG. 4 are embedded in a shared enclosure 30. FIG. 4 indicates the "notional" separation lines 44 between the individual detector circuits 20. Using the shared enclosure 30 for a plurality of ASICs 22 can increase the precision of the mutual alignment of the individual ASICs 22 (and in the case of a plurality of adjacent sensor elements 10, thus also the mutual alignment of these sensor elements 10).

In an optional example embodiment, which is not presented in greater detail, (likewise described with reference to FIG. 4), a plurality of separate sensor elements 10 are applied to the ASICs 22 embedded in the shared enclosure 30.

Figure 5:
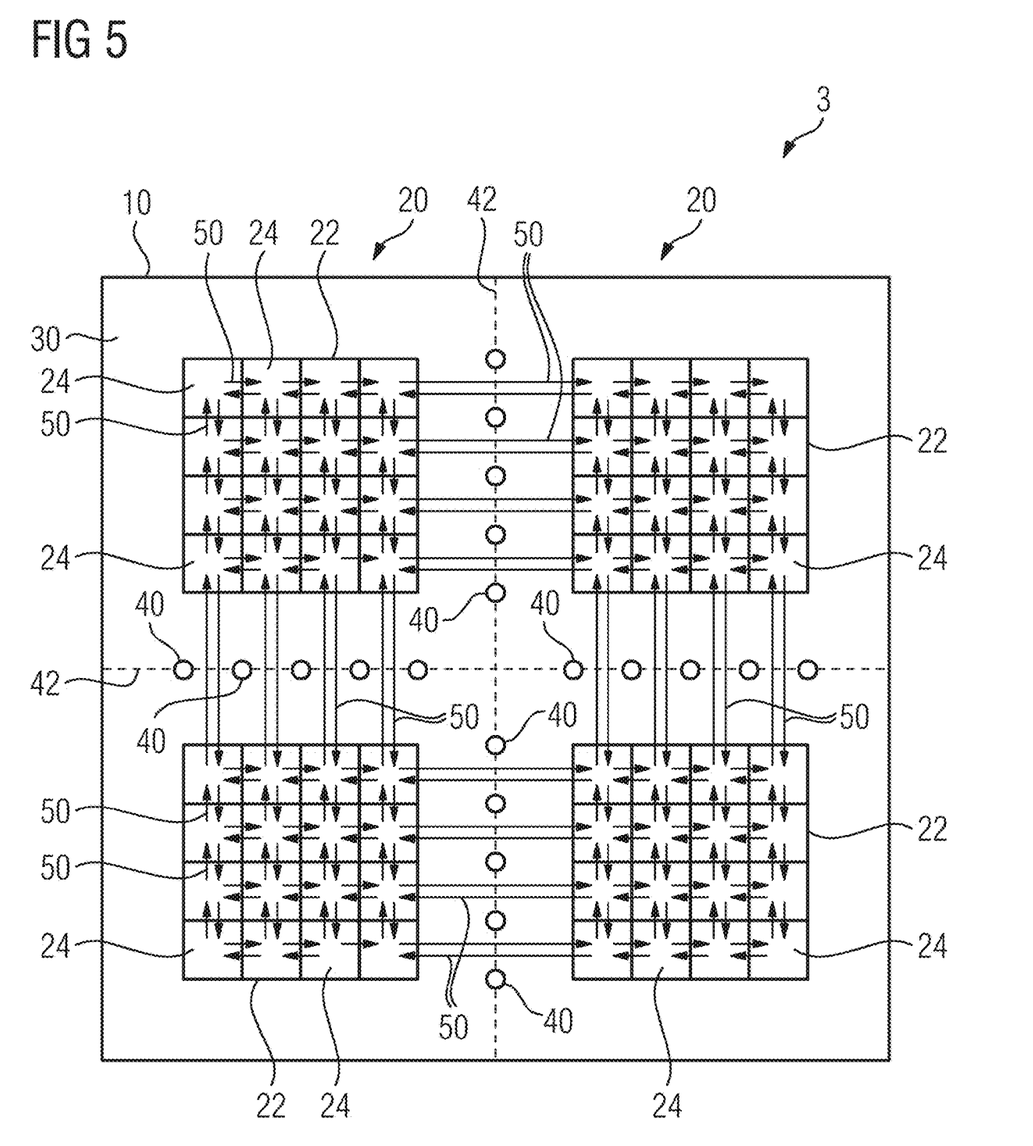
FIG. 5 is a view corresponding to FIG. 3 again of a further example embodiment of the X-ray radiation detector.

FIG. 5 shows a development of the X-ray detector 3 described in FIG. 4. The X-ray detector 3 is here configured and intended for identifying what are known as charge-sharing events. For this purpose, the individual detector pixels 24 of each ASIC 22, specifically the detector pixels 24 arranged side by side, are in signal communication contact with one another. In FIG. 5, this contact is indicated in each case by a pair of arrows 50 pointing in opposite directions. In an optional example embodiment, which is not presented in greater detail, the diagonally adjacent sensor pixels 12 are also in contact with one another.

In the example embodiment shown in FIG. 5, the contact redistribution layer 34 extends across the notional separation lines 44 between the various detector circuits 20, across the entire shared enclosure 30 of all the ASICs 22 embedded therein (2×2 ASICs 22 in the example embodiment shown). In order now to be able to identify also charge-sharing events between the sensor pixels 12 of sensor elements 10 that are mutually adjacent and formed separately from one another, the detector pixels 24 of mutually adjacent ASICs 22 are likewise signal-communicatively connected to one another by way of the contact redistribution layer 34. This can increase the accuracy of identifying charge-sharing events and thus can increase the precision of the X-ray detector 3 during intended use of the X-ray apparatus 1.

Figure 7:
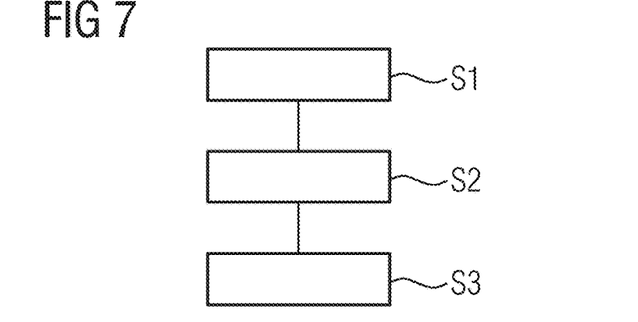
FIG. 7 is a schematic flow diagram of a method for producing the X-ray radiation detector.

FIG. 7 shows schematically a method for producing the X-ray detector 3 comprising at least one sensor element 10 and a detector circuit 20 situated after the sensor element 10 in the direction of incident radiation.

First, in a step S1, at least one sensor element 10 is provided, wherein the sensor element 10 is formed by a semiconductor material and is sensitive to incident radiation, and wherein the sensor element 10 forms a pixel array comprising a number of sensor pixels 12.

In a further method step S2, the detector circuit 20 is provided, wherein the detector circuit 20 is used to detect charge carriers generated in the semiconductor material of the sensor element 10 as a result of radiation, and comprises an integrated circuit 22 comprising a number of detector pixels 24, wherein a surface dimension of the integrated circuit 22 is smaller than the surface dimension of the sensor element 10 by more than one pixel width of the sensor pixels 12.

In a further step S3, the detector pixels 24 are placed in signal communication contact with the sensor pixels 12 by way of a contact redistribution layer 34 arranged on an enclosure 30, in which the integrated circuit 22 is embedded.

In a further method step, which can take place in parallel with the method step S1 or earlier or later, a plurality of ASICs 22 provided for a single sensor element 10 (as described above by way of example with reference to FIG. 4) are grouped together in the shared enclosure 30. In the method step S3, the ASICs 22 grouped together by the shared enclosure 30 are mounted on the sensor element 10, and the sensor pixels 12 that correspond to one another are placed in contact with the detector pixels of the respective ASICs 22 (indirectly by way of the solder balls 26 and the conductor tracks 36 of the contact redistribution layer 34).

In a variant of the production method described above, more ASICs 22 than are needed for a single sensor element 10 (for example 4 times, 6 times, 10 times the number, or a larger number) are grouped together in the shared enclosure 30 to form a "detector circuit array". In the method step S3, a plurality of individual sensor elements 10 (so for example 4, 6, 10, etc.) are then placed on this detector circuit array. Contact is then made from the respective sensor pixels 12 to the detector pixels of the individual ASICs 22 again in a similar way to that described above.

The subject of the invention is not restricted to the above-described example embodiments. In fact a person skilled in the art can derive further embodiments of the invention from the above description. In particular, the individual features of the invention and its embodiment variants, which features are described with reference to the various example embodiments, can also be combined with one another in different ways.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A photon detector, comprising:
   at least one sensor element, formed by a semiconductor material and sensitive to incident radiation, the at least one sensor element forming a pixel array and including a number of sensor pixels; and
   a detector circuit, situated after the at least one sensor element in a direction of incident radiation, to detect charge carriers generated in the semiconductor material of the sensor element as a result of radiation, wherein the detector circuit includes an integrated circuit including a number of detector pixels, the number of detector pixels being in signal communication contact with the number of sensor pixels,
   wherein a surface dimension of the integrated circuit is relatively less than a surface dimension of the sensor element by more than one pixel width of the number of sensor pixels,
   wherein the detector circuit includes
      an enclosure, surrounding the integrated circuit, the integrated circuit being embedded in the enclosure and a pixel face being formed on the enclosure, the pixel face facing the at least one sensor element, and
      a contact redistribution layer, contact pads being formed in the contact redistribution layer for signal-communicatively connecting respective detector pixels, of the number of detector pixels, to correspondingly assigned sensor pixels of the number of sensor pixels, and conductor tracks being formed in the contact redistribution layer, for connecting the contact pads to the number of detector pixels of the integrated circuit.

2. The photon detector of claim 1, wherein the integrated circuit is embedded in the enclosure, flush with a surface of the enclosure and without any gaps along edges of the enclosure.

3. The photon detector of claim 2, wherein the contact redistribution layer is formed by a thin film application process.

4. The photon detector of claim 2, wherein the detector circuit, through the integrated circuit, is fabricated by fan-out wafer-level chip-scale packaging.

5. The photon detector of claim 1, wherein the contact redistribution layer is formed by a thin film application process.

6. The photon detector of claim 1, wherein the detector circuit, through the integrated circuit, is fabricated by fan-out wafer-level chip-scale packaging.

7. The photon detector of claim 1, wherein the detector circuit includes, in a region of the enclosure, at least one via for the signal communication connection to a subsequent control and at least one of an analysis unit and a subsequent signal-routing device.

8. The photon detector of claim 1, wherein a plurality of detector circuits are assigned to a sensor element, of the at least one sensor element, and make contact with the sensor element in a grid formation, so that each integrated circuit is connected to a separately assigned group of the number of sensor pixels of the at least one sensor element.

9. The photon detector of claim 1, wherein the at least one sensor element includes a plurality of sensor elements and the detector includes at least two detectors, the plurality of sensor elements being arranged side by side and each of the plurality of sensor elements including a plurality of correspondingly assigned detector circuits of the at least two detector circuits, and wherein a respective enclosure of each of at least two respective detector circuits, of the at least two detector circuits, are formed together integrally.

10. The photon detector of claim 9, wherein at least two sensor elements of the plurality of sensor elements, arranged side by side, are joined to a plurality of detector circuits integrally joined via a respective enclosure.

11. The photon detector of claim 9, wherein the enclosure of each of at least two detector circuits are formed together monolithically.

12. The photon detector of claim 11, wherein at least two sensor elements of the plurality of sensor elements, arranged side by side, are joined to a plurality of detector circuits integrally joined via a respective enclosure.

13. The photon detector of claim 1, wherein the detector circuit is configured to identify a charge-sharing event, by adjacent detector pixels, of the number of detector pixels, of the integrated circuit being signal-communicatively interconnected.

14. The photon detector of claim 13, wherein, to identify the charge-sharing event, detector pixels of two integrated circuits, arranged side by side in integrally joined enclosures and facing one another along edges, are signal-communicatively connected to one another via the contact redistribution layer of the enclosure.

15. The photon detector of claim 14, wherein the two integrated circuits arranged side by side by integrally joined enclosures, and are signal-communicatively connected using the contact redistribution layer of the enclosure.

16. A medical X-ray apparatus, comprising:
   the photo detector of claim 1.

17. The medical X-ray apparatus of claim 16, wherein the medical X-ray apparatus is a computed tomography apparatus.

18. The photon detector of claim 1, wherein the photo detector is an X-ray radiation detector.

19. The photon detector of claim 1, wherein the at least one sensor element includes a plurality of sensor elements and wherein a plurality of detector circuits are assigned to a sensor element, of the plurality of sensor elements, and make contact with the sensor element in a grid formation, so that each integrated circuit is connected to a separately assigned group of the number of the sensor element.

20. A medical X-ray apparatus, comprising:
   the x-ray radiation detector of claim 18.

21. The medical X-ray apparatus of claim 20, wherein the medical X-ray apparatus is a computed tomography apparatus.

22. A method for producing a photon detector including at least one sensor element and a detector circuit, the detector circuit being situated after the sensor element in a direction of incident radiation, the method comprising:
   providing at least one sensor element, the at least one sensor element being formed by a semiconductor material and being sensitive to incident radiation, wherein the at least one sensor element forms a pixel array including a number of sensor pixels;

providing the detector circuit, the detector circuit being used to detect charge carriers generated in the semiconductor material of the at least one sensor element as a result of radiation, and the detector circuit including an integrated circuit including a number of detector pixels, a surface dimension of the integrated circuit being relatively smaller than a surface dimension of the at least one sensor element by more than one pixel width of the number of sensor pixels; and placing the detector pixels in signal communication contact with the sensor pixels via a contact redistribution layer arranged on an enclosure, the integrated circuit being embedded on the enclosure.

23. The method of claim 22, wherein the detector circuit includes the integrated circuit and is fabricated by fan-out wafer-level chip-scale packaging.

* * * * *